US009880037B2

(12) United States Patent
Babin et al.

(10) Patent No.: US 9,880,037 B2
(45) Date of Patent: Jan. 30, 2018

(54) METHOD AND SYSTEM FOR MONITORING EMISSIONS FROM AN EXHAUST STACK

(71) Applicant: INSTITUT NATIONAL D'OPTIQUE, Québec (CA)

(72) Inventors: François Babin, Québec (CA); Jean-François Gravel, Québec (CA)

(73) Assignee: INSTITUT NATIONAL D'OPTIQUE, Quebec (CA)

( * ) Notice: Subject to any disclaimer, the term of this patent is extended or adjusted under 35 U.S.C. 154(b) by 321 days.

(21) Appl. No.: 14/938,955

(22) Filed: Nov. 12, 2015

(65) Prior Publication Data

US 2016/0131514 A1    May 12, 2016

Related U.S. Application Data

(60) Provisional application No. 62/078,678, filed on Nov. 12, 2014.

(51) Int. Cl.
| | | |
|---|---|---|
| *G01N 21/85* | (2006.01) | |
| *G01F 1/86* | (2006.01) | |
| *G01N 21/65* | (2006.01) | |
| *G01N 21/39* | (2006.01) | |
| *G01N 21/53* | (2006.01) | |

(Continued)

(52) U.S. Cl.
CPC ............... *G01F 1/86* (2013.01); *G01N 21/39* (2013.01); *G01N 21/53* (2013.01); *G01N 21/6456* (2013.01); *G01N 21/65* (2013.01); *G01N 2021/1793* (2013.01); *G01N 2021/399* (2013.01); *G01N 2021/536* (2013.01)

(58) Field of Classification Search
CPC .......... G01F 1/86; G01N 21/39; G01N 21/53; G01N 21/6456; G01N 2021/1793; G01N 2021/399; G01N 2021/536
USPC ........................................................ 356/410
See application file for complete search history.

(56) References Cited

U.S. PATENT DOCUMENTS

| 3,768,908 A | 10/1973 | Zaromb |
| 4,362,388 A | 12/1982 | Egan et al. |

(Continued)

OTHER PUBLICATIONS

VDI (The Association of German Egineers), "Remote sensing—Atmospheric measurements with LIDAR—Measuring gaseous air pollution with DAS LIDAR", VDI 4210, Part 1, Jun. 1999, 47 pages, 4210, Verein Deutscher Ingenieure, Dusseldorf.

*Primary Examiner* — Mark Hellner
(74) *Attorney, Agent, or Firm* — Fasken Martineau Dumoulin LLP

(57) ABSTRACT

There is described a method for remotely monitoring an exhaust plume emitted by an exhaust stack, the method comprising: determining a velocity of a flow of the exhaust plume at an output of the exhaust stack, the exhaust plume comprising one molecule; propagating a first light within the exhaust plume, the first light being propagated in close proximity to the output of the exhaust stack; detecting a second light emitted by the exhaust plume and measuring an energy of the second light, the second light resulting from an interaction of the first light with the exhaust plume; and determining a mass emission rate of the at least one molecule using the measured energy of the detected second light, the velocity, and a surface area of the exhaust plume at the output of the exhaust stack, the surface area being orthogonal to a direction of the flow of the exhaust plume.

16 Claims, 4 Drawing Sheets

(51) Int. Cl.
*G01N 21/64* (2006.01)
*G01N 21/17* (2006.01)

(56) References Cited

U.S. PATENT DOCUMENTS

| | | | | |
|---|---|---|---|---|
| 5,440,937 A | * | 8/1995 | Lynnworth | G01F 1/662 |
| | | | | 73/861.25 |
| 5,672,827 A | * | 9/1997 | Jursich | G01F 1/704 |
| | | | | 73/861.07 |
| 6,384,903 B1 | * | 5/2002 | Fuller | G01J 3/42 |
| | | | | 356/301 |
| 2002/0059033 A1 | * | 5/2002 | Batug | G01N 1/2258 |
| | | | | 702/24 |
| 2014/0336953 A1 | * | 11/2014 | Johnson | G01N 21/538 |
| | | | | 702/24 |

* cited by examiner

METHOD AND SYSTEM FOR MONITORING EMISSIONS FROM AN EXHAUST STACK

TECHNICAL FIELD

The present invention relates to the field of methods and systems for monitoring emissions from an exhaust stack, and more particularly methods and systems for remotely monitoring molecules contained in emissions from an exhaust stack.

BACKGROUND

The burning of fuels such as natural gas, oil or coal in power plants, pipeline compressor stations or flares generates polluting emissions. The exhaust from the burning of the fuels is usually evacuated through an exhaust stack or duct, which usually takes the form of a chimney. Most of environmental protection agencies worldwide regulate the emissions from these exhaust stacks or ducts. Standardized methods exist for measuring parameters such as the mass emission rates of molecules such as $NO_R$, $CO$, $CO_2$, $SO_2$, particulate matter and/or the like.

Most of these standardized methods rely on sampling part of the exhaust stream inside the stack or duct. A probe head is inserted into the stream through a sampling port. Usually, there is more than one port on those stacks that have sampling ports. These sampling ports are used for measuring gas flow velocity, ascertaining that the flow is substantially constant across the entire stack cross section, and verifying that the sampling location is representative of the entire stream. Sampling with the probes is very much localized inside the stream. In some cases, the probe samples the exhaust gas which is routed through tubing and other apparatus to a measurement instrument that is calibrated for concentration measurements of different molecules or particulates. The measurement instruments are usually based on optical principles.

There are also alternative techniques to localized sampling of the exhaust stream. Such alternative techniques, such as integrated path continuous emissions monitoring (IP-CEM) techniques, allow measurements across the entire stack stream and do not require any sampling of part of the stack gas or any routing of the samples to the measurement instrument. However, these alternative measurement techniques also require the presence of ports with mounting flanges. An example of an IP-CEMS method is the US EPA PS-18.

Mounting instruments or inserting probes through sampling ports requires that there be sampling ports on the stack or duct, which is not always the case. A technique is thus required to monitor emissions without the use of sampling ports. In addition, mounting instruments or inserting probes usually has an impact on operations. In order to insert or install probes and instruments, the evacuation of hot and noxious emissions through the stack or duct must be halted, having a detrimental impact on operations. Moreover, having personnel working around the exhaust stacks or ducts and on the premises requires special training and oversight.

Such a remote monitoring method exists for remotely monitoring point sources such as exhaust stacks or ducts. This remote monitoring method relies on a differential absorption light detection and ranging (lidar) apparatus (DIAL) away from the stack or duct. The emissions are allowed to disperse in the atmosphere and form a large plume that is carried by the wind. A pulsed laser is sent across the plume and the backscattered laser light is measured through a receiver telescope. The amount of backscattered light is measured with respect to time after the emission of the laser pulse, which gives a spatially resolved measurement along the beam propagation axis. The amount of backscattered light depends on the attenuation of the laser beam along its axis of propagation which in turns depends on the scattering from particulates and molecules, and on the absorption by molecules. The wavelengths of light for which there is measurable absorption is different for each molecule and constitutes a fingerprint for the molecule. By measuring backscatter light at a number of wavelengths of which at least one wavelength is significantly absorbed by the targeted molecule, a map of the concentration of the molecule can be built through the spatially resolved measurement of the backscattered light along the laser beam propagation axis and by scanning the laser beam across a volume of space. By building a concentration map in a plane perpendicular to the wind direction, and measuring the wind speed, mass emission rates of pollutants can be computed. This is described in detail in VDI 4210, a German standard for emissions measurements using a lidar system. This approach requires that the lidar system be positioned at a relatively large distance from the stack, commensurate with dispersed plume size, and measure small concentration-length products in the dispersed plume, and consequently it will use a large laser with a consequent amount of power and a large receiving telescope and large scanning optics, all of which are mounted on a large mobile platform. This approach is seldom used because there are but a few of these systems that have been built and they are complicated and expensive to use and cannot be driven to many of the remote sites that need to be monitored. And also, they depend on stable wind, in direction and strength. In addition, the spatial resolution is seldom below 5 meters, because of laser pulse length and the necessary large volumes that need to be probed for the detection of the very low concentrations in the dispersed plume. In addition, mixing with the atmospheric air needs to be considered and corrected for.

Therefore, there is a need for an improved method and system for remotely monitoring molecules contained in emissions from an exhaust stack.

SUMMARY

In accordance with a first broad aspect, there is provided a method for remotely monitoring an exhaust plume emitted by an exhaust stack, the method comprising: determining a velocity of a flow of the exhaust plume at an output of the exhaust stack, the exhaust plume comprising emissions, the emissions comprising at least one molecule; remotely propagating a first light within the exhaust plume emitted by the exhaust stack, the first light being propagated in close proximity to the output of the exhaust stack; remotely detecting a second light emitted by the exhaust plume present in close proximity to the output of the exhaust stack and measuring an energy of the detected second light, the second light resulting from an interaction of the first light with the emissions contained within the exhaust plume; determining a mass emission rate of the at least one molecule contained in the exhaust plume using the measured energy of the detected second light, the velocity of the flow of the exhaust plume, and a surface area of the exhaust plume at the output of the exhaust stack, the surface area being orthogonal to a direction of the flow of the exhaust plume; and outputting the determined mass emission rate.

In one embodiment, the surface area of the exhaust plume substantially corresponds to a surface area of the output of the exhaust stack.

In another embodiment, the surface area of the exhaust plume is taken in a plane substantially perpendicular to a direction of the flow of the exhaust plume In one embodiment, the step of determining the velocity comprises measuring the velocity within the exhaust stack using a flow velocity sensor installed within the exhaust stack.

In another embodiment, the step of determining the velocity comprises measuring the velocity outside the exhaust stack in a region being in close proximity to the output of the exhaust stack.

In one embodiment, the step of measuring the velocity is remotely and optically performed.

In one embodiment, wherein the exhaust stack is connected to a combustion chamber in which a mixture of fuel and air is burnt and said determining the velocity comprises calculating the velocity using at least a flow rate of the fuel delivered to the combustion chamber, a flow rate of the air delivered to the combustion chamber, a composition of the fuel, and a temperature within the combustion chamber.

In one embodiment, the step of detecting the second light comprises detecting the second light that propagates back towards a transceiver adapted to emit the first light and detect the second light.

In one embodiment, the step of detecting the second light comprises imaging the second light in the exhaust plume being in close proximity to the output of the exhaust stack.

In one embodiment, the first and second lights each comprise one of a pulsed light, a continuous light, and a continuous modulated light.

In one embodiment, the step of determining the mass emission rate comprises: determining a differential optical absorption of the first light being in close proximity to the output of the exhaust stack; determining a concentration of the at least one molecule using the differential optical absorption; and determining the mass emission rate using the concentration, the velocity of the flow of the exhaust plume, and the surface area of the exhaust plume.

In one embodiment, the step of determining the absorption is performed using a differential absorption lidar.

In another embodiment, the step of determining the absorption is performed using one of a fluorescence lidar and a Raman lidar.

In one embodiment, the step of detecting said second light comprises detecting Raman scattered light generated by the exhaust plume while interacting with the first light being propagated in close proximity to the output of the exhaust stack, and said determining the mass emission rate comprises: determining a concentration of the at least one molecule using relative Raman scattered light energies; and determining the mass emission rate using the concentration, the velocity of the flow of the exhaust plume, and the surface area of the exhaust plume.

In one embodiment, the step of detecting said second light comprises detecting fluorescence light generated by the exhaust plume while interacting with the first light being propagated in close proximity to the output of the exhaust stack, and said determining the mass emission rate comprises: determining a concentration of the at least one molecule using fluorescence energy relative to a local excitation energy; and determining the mass emission rate using the concentration, the velocity of the flow of the exhaust plume, and the surface area of the exhaust plume.

In accordance with another broad aspect, there is provided a system for remotely monitoring an exhaust plume emitted by an exhaust stack, the system comprising: a flow velocity unit for determining a velocity of a flow of the exhaust plume at an output of the exhaust stack, the exhaust plume comprising emissions, the emissions comprising at least one molecule; a light source for generating a first light, the light source being adapted to propagate the first light within a portion of the exhaust plume emitted by the exhaust stack being in close proximity to the output of the exhaust stack; a light detection device for detecting a second light emitted by the exhaust plume present in close proximity to the output of the exhaust stack and measuring an energy of the detected second light, the second light resulting from an interaction of the first light with the emissions contained within the exhaust plume; and a calculation module for determining a mass emission rate of the at least one molecule contained in the exhaust plume using the measured energy of the detected second light, the determined velocity of the flow of the exhaust plume, and surface area of the exhaust plume at the output of the exhaust stack, the surface area being orthogonal to a direction of the flow of the exhaust plume, and outputting the determined mass emission rate.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

The system and method presented herein allow for remotely and optically monitoring molecules contained in emissions using spatially resolved techniques, such as lidar. The emissions comprise all elements that are emitted from an exhaust stack such as a gas, a liquid and/or a solid. Liquid or solid particulates may be present in the emissions from the stack. The monitoring is performed in a region being in close proximity to the output of the stack or duct from which an emissions stream such as a gas and particulates stream is emitted (hereinafter referred to as the close proximity region), thereby forming a plume. In one embodiment, the close proximity region is defined as the region being adjacent the output of the stack and in which the plume has substantially not been dispersed yet. In the same or another embodiment, the close proximity region is defined as the region being within about 30 cm from the stack output. In a further embodiment, the close proximity region is defined as the region being within about $1/5^{th}$ of the diameter of the stack cross-section from the stack output, if the stack output has a circular cross-sectional shape, or within $1/5^{th}$ of the greatest dimension of the cross-section of the stack output if the stack output is not circular. The portion of the plume located in close proximity to the output of the stack is usually well confined, and the cross-sectional surface area of the plume perpendicular to the flow direction usually covers substantially the same cross-sectional surface area as that of the stack output. Therefore, scanning across the plume may not be necessary if the local mass emission rate measurement is representative of the total emissions output. However, the person skilled in the art will understand that scanning across the plume may be performed in some embodiments in order to obtain the mass emission rate of a given molecule. In addition, the emissions flow velocity within the region located in close proximity to the output of the stack usually does not depend on wind. In an embodiment in which the stream of emissions within the stack is stable in time, the output stream of emissions is substantially stable in time within the region located in close proximity of the output of the stack so that signal accumulation over extended periods of time may be possible.

Figure 1:
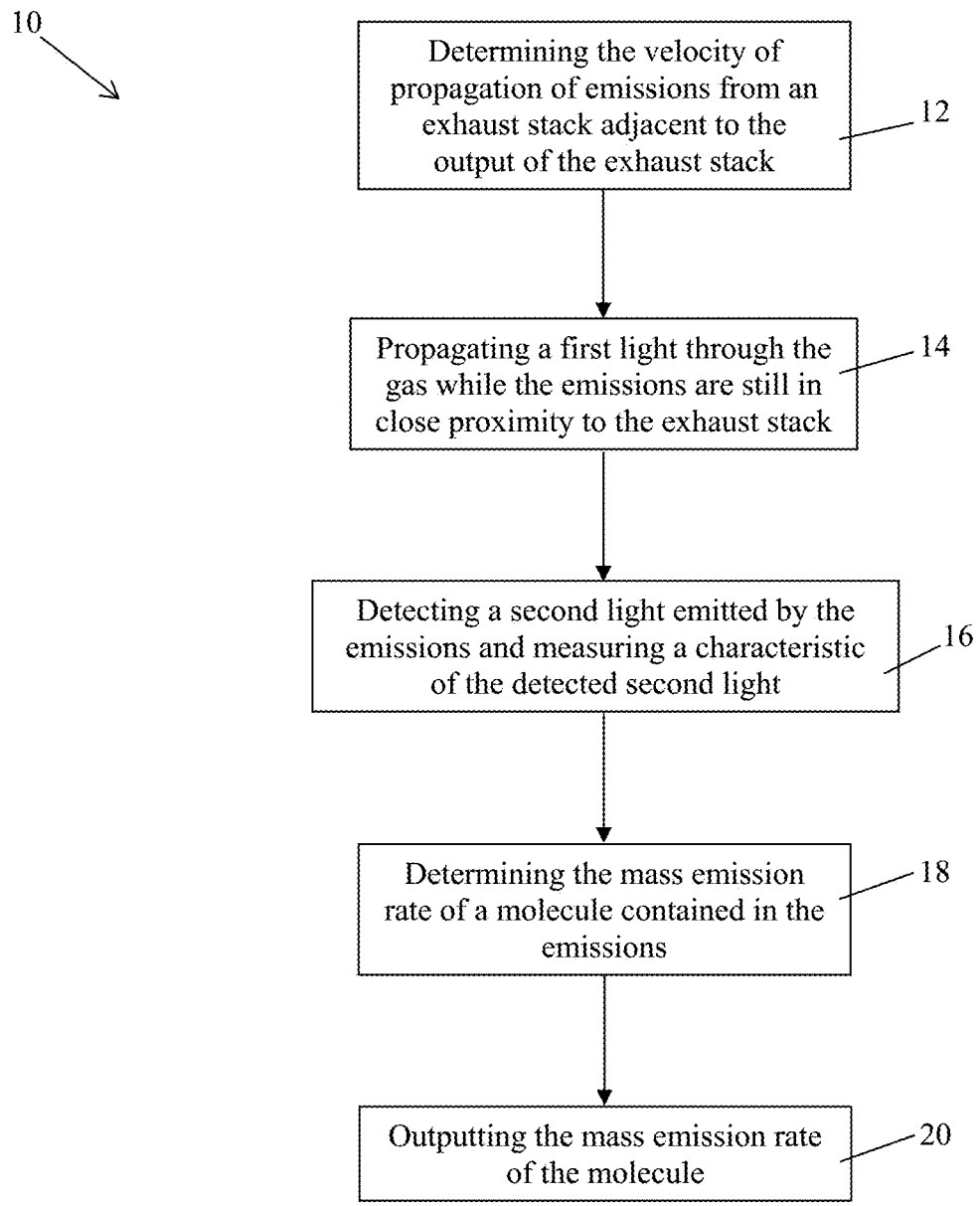
FIG. 1 is a flow chart of a method for remotely monitoring mass emission rates of molecules contained in emissions from a stack, in accordance with an embodiment.

FIG. 1 illustrates an embodiment of a method 10 for remotely monitoring molecules contained in emissions from a stack. It should be understood that a stack may be any adequate exhaust device in which emissions may propagate to be evacuated from a structure. For example, a stack may be a duct, a chimney, a flare, or the like. The stack may emerge substantially vertically from a structure such as a power plant, a pipeline compressor station, etc. In another embodiment, the stack may emerge from the structure along an axis other than a vertical axis such as a horizontal axis.

At step 12, the velocity of the emissions exiting the stack output is determined. In an embodiment in which the emissions comprise a gas and particulates, it should be understood that the velocity of the particulates is substantially equal to that of the gas. In one embodiment, the velocity of the emissions stream is measured within the stack in a region adjacent to the output of the stack for example. In this case, a velocity sensor adapted to measure the velocity of the emissions stream is inserted into the stack at any adequate position therein. For example, a pitot tube, a differential pressure gauge, an optical flow sensor, an ultrasonic flow sensor, or the like may be used for measuring the velocity of the emissions.

In another embodiment, the velocity of the emissions stream is measured outside of the stack in a region being located in close proximity to the stack output. The velocity of the emissions stream located in close proximity of the stack output may be measured remotely using any adequate optical method. For example, image correlation techniques, turbulence analysis techniques, transverse Doppler techniques, or the like may be used for remotely determining the velocity of the emissions. Alternatively, a velocity sensor may be positioned outside of the stack at an adequate position within the close proximity region for sensing the emissions velocity within the region being in close proximity to the stack output.

In an embodiment in which the stack is used for outputting an emissions stream resulting from the combustion of a fuel, the velocity of the emissions stream may be determined from calibrated measurements of the flow rate of the fuel provided to the combustion chamber, composition and energy content of the fuel along with a measurement of the excess oxygen concentration and the combustion temperature, as known in the art.

Figure 2:
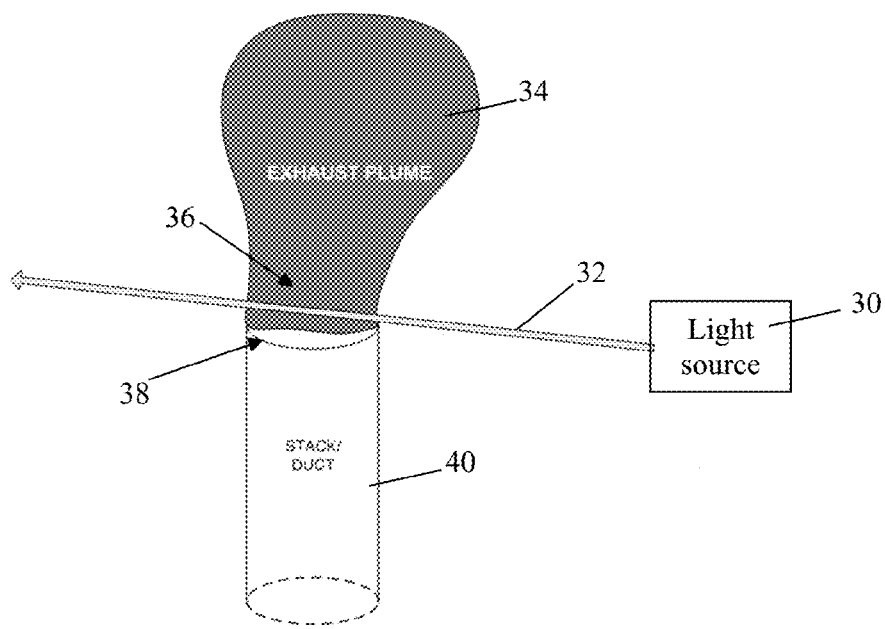
FIG. 2 illustrates a system for remotely monitoring mass emission rates of molecules contained in emissions from a stack using backscattered light, in accordance with an embodiment.

At step 14, light is propagated across the exhaust plume within the region being in close proximity to the stack output. As illustrated in FIG. 2, a light source 30 emits a light beam 32 and the light source 30 is adapted to propagate the emitted light beam 32 across at least a portion of the plume 34 within the region 36 being in close proximity to the output 38 of the stack 40 so that the path of the emitted light beam 32 intersects the surface area of the plume 34. In one embodiment, the light beam 32 is directed so as to substantially intersect with the center of the plume.

The light source 30 may be any adequate light emitter adapted to create and propagate a beam of light. The light source 30 may comprise optics such as lenses to form the beam of light. The light source may comprise a laser, a lamp such as a filament lamp or a gas discharge lamp, a light emitting diode, an amplified spontaneous emission light source, or the like.

In one embodiment, the location of the light source 30 with respect to the output 38 of the stack 40 is chosen so that the beam of light 32 propagates at a minimal distance from the output 38 of the stack 40. For example, the light source 30 may be secured to the ground. Alternatively, the light source 30 may be secured to a structure or a platform so as to be at a certain height from the ground. In one embodiment, the light source 30 is positioned to be substantially at a same height relative to the ground as that of the output 38 of the stack 40. It should be understood that the light source 30 is placed remotely from the stack 40. For example, the light source 30 may be located between 40 to 50 meters away from the stack 40. When the stack is a part of a pipeline compressor station, the light source 30 may be located outside the fence enclosing the pipeline compressor station.

While propagating within the plume, the light interacts with the molecules and/or particulates contained therein. The interaction of the light with the molecules and/or particulates contained within the emanation/plume from the stack output creates a second light which may be seen as being emitted by the gas/particulates contained in the region of the plume being in close proximity to the stack output. For example, the beam of light 32 emitted by the light source 30 may be scattered by the molecules and/or particulates contained in the plume. In this case, the second light is formed of the scattered light. The light 32 emitted by the light source 30 may also generate fluorescence or phosphorescence while interacting with the molecules and/or particulates contained in the plume. In this case, the second light comprises the fluorescence or phosphorescence light. It should be understood that more than one physical interaction may occur between the emitted light 32 and the molecules and/or particulates so that the second light may contain scattered light and fluorescence and/or phosphorescence light for example. Molecules and particulates may scatter light all along the light beam path, through Rayleigh or Mie scattering. Molecules and particulates may further fluoresce or phosphoresce. Molecules and particulates may also generate Raman scattering, and in particular ultraviolet (UV) enhanced or resonant Raman scattering. The person skilled in the art will understand that other interaction phenomena may also occur.

It should be understood that the system 10 comprises a light detector for detecting the second light. In the embodiment illustrated in FIG. 2, the light detector is integrated with the light source 30 which may be a lidar adapted to emit light and detect backscattered light. In another embodiment, the light detector may be independent from the light source 30 and positioned at any adequate positon to detect the second light.

Referring back to FIG. 1, the second light is detected at step 16 and the energy of the detected second light is measured. In one embodiment, the energy of the second light at at least one wavelength is measured. It should be understood that any adequate light detector may be used.

At step 18, the mass emission rate of the molecules contained in the emissions is determined. Particularly, the mass emission rate of a given molecule is determined. The concentration of the given molecule is first determined using the measured energy of the second light. Then, the mass emission rate of the given molecule is determined from the concentration of the given molecule, the measured or determined velocity of the emissions stream within the region being in close proximity to the stack output 38, and the cross-sectional surface area of the plume perpendicular to the flow direction where the measurement is done. In one embodiment, the surface area of the plume is assumed to be substantially equal to the surface area of the stack. The mass emission rate E may then be determined using the following equation:

$$E = K*C*V*A$$

where K is a species-specific constant, C is the molecule concentration, V is the velocity of the emissions stream, and A is the surface area of the plume or the stack.

Finally, the determined mass emission rate is outputted at step 20. For example, the determined mass emission rate may be stored locally or remotely in a memory. In another example, the determined emission rate may be sent to a display unit to be displayed thereon.

It should be understood that the optical spectrum of the first light and the optical spectral response of the light detector that detects the second light are chosen as a function of at least one given molecule of which the mass emission rate is to be determined. The optical spectrum of the first light and the optical spectral response of the light detector that detects the second light are further chosen as a function of the type of interaction to be monitored between the first light and the given molecule to be sensed.

In one embodiment, Raman scattering is considered and therefore the method 10 uses a Raman lidar for determining the mass emission rate. In this case, the light source 30 illustrated in FIG. 2 comprises a Raman lidar. The first light preferably comprises one excitation wavelength from a light source such as a laser with a spectral linewidth smaller than 0.1 nm. In the case of a Raman lidar, the wavelength of the first light can be any wavelength from the ultraviolet (UV) to the near infrared (IR), but preferably a UV wavelength. In the case of a Raman lidar, it should be understood that the energy at more than one detection wavelength may be measured. The excitation wavelength and the detection wavelength(s) are chosen as a function of the Raman scattering signature or fingerprint of the given molecule to be sensed. The concentration of the given molecule may be determined by knowing the initial energy at the excitation wavelength and at the location where the second light is detected and the measured energy relative to the excitation energy at the detection wavelength(s) using any adequate method known in the art.

In another embodiment, fluorescence is considered and therefore the method 10 uses a fluorescence lidar for determining the mass emission rate. In this case, the light source 30 illustrated in FIG. 2 comprises a fluorescence lidar. The first light comprises at least one excitation wavelength that is adapted to create fluorescence when interacting with the given molecule to be sensed, and the second light comprises at least one detection wavelength that corresponds to that of the generated fluorescence light. It should be understood that the light source 30 may emit light at more than one excitation wavelength for generating fluorescence, and the energy at more than one detection wavelength may be measured. The excitation wavelength(s) is chosen to generate fluorescence and the detection wavelength(s) are chosen as a function of the fluorescence signature or fingerprint of the given molecule to be sensed. The concentration of the given molecule may be determined by knowing the initial energy at the excitation wavelength(s) and at the location where the second light is detected and the measured energy at the detection fluorescence wavelength(s) relative to the excitation energy at the detection wavelength(s) using any adequate method known in the art, and the fluorescence quantum yield.

In the case of NO and $NO_2$, measurements can be done with a fluorescence lidar. Prior art literature tends to teach that at atmospheric pressure, fluorescence from molecules is strongly quenched. However, it is not the case for NO and $NO_2$. In special cases, measuring molecular concentrations with a fluorescence lidar is possible in the exhaust plume from an exhaust stack within the close proximity region.

In a further embodiment, absorption is considered and the method 10 uses absorption measurements for determining the mass emission rate. In an embodiment of the absorption measurement method, elastic scattering is considered and the method 10 uses a usual two-wavelength DIAL technique comprising an ON absorption wavelength and an OFF absorption wavelength. The OFF absorption wavelength is used to measure the scattering while the ON absorption wavelength is used for measuring both the scattering and the absorption. In another embodiment of the absorption method, the absorption is determined from the rate of fall with distance of fluorescence. In this case, the first light comprises an ON wavelength that is used for measuring the rate of fall with distance of fluorescence in order to obtain both absorption and scattering losses, and a second and different wavelength, i.e. the OFF wavelength, is used to measure the Raman rate of fall with distance of nitrogen in order to obtain the scattering losses. The absorption may then be determined from the measurements at the two wavelengths. In a further embodiment of the absorption method Raman scattering is considered, the absorption is determined from the rate of fall with distance of the Raman of nitrogen. In this case, the first light comprises an ON wavelength that is used for measuring the rate of fall with distance of the Raman of nitrogen in order to obtain both absorption and scattering losses, and a second and different wavelength, i.e. the OFF wavelength, is used to measure the Raman rate of fall with distance of nitrogen in order to obtain the scattering losses. The absorption may then be determined from the measurements at the two wavelengths. It should be understood that the measurement system comprises a calculation module (not shown) that comprises at least a processing unit, a memory, and a communication unit. The calculation unit is in communication with at least the velocity sensor for receiving the measured velocity of the emissions stream therefrom and the light detector for receiving the measured energy of the second light therefrom. Alternatively, the calculation unit is provided with a user interface that may be used by a user to input the value of the velocity. The calculation unit may further be in communication with the light source 30 in order to receive the value of the energy of the first light therefrom. The calculation module is adapted to calculate the mass emission rate using the measured energies of the second light, the measured velocity of the emissions stream, and the surface area of the plume at the stack output. The calculation module is further adapted to output the determined mass emission rate. For example, the mass emission rate may be stored in memory. In another example, the mass emission rate may be transmitted to a remote machine such as a remote server over a telecommunication network. In still another example, the mass emission rate may be sent to a display unit to be displayed thereon.

In one embodiment, the second light that propagates back towards the apparatus containing the light source 30 is measured. For example, the second light may correspond to backscattered light. In this case, a light detector is positioned within the transceiver apparatus along with the light source 30. The light detector may be coupled to light gathering and imaging optics, thereby forming a receiver. For example, an optical transceiver may be used for both emitting the first light and detecting the second light. In one embodiment, the first light emitted by the light source 30 is pulsed so that the second light is also pulsed. In this case, the light detector is adapted to detect pulses of light having at least one predefined wavelength.

In order to detect the scattering, fluorescence, phosphorescence, and/or the like from molecules and particulates present in the exhaust stream, the scattering, fluorescence, phosphorescence, and/or the like occurring from molecules and particulates located outside the exhaust stream must be isolated. This can be done by using temporal time of flight techniques. The first light comprises a series of short light pulses that interact with the molecules and particulates. This interaction locally causes return pulses of scattering and fluorescence, i.e. the second light. The return pulses are detected with a detector adapted to temporally resolve the short light pulses or a gated detector that may isolate the return pulses from a volume substantially equivalent in length to the light pulse duration multiplied by the velocity of light. The arrival of the return pulses at the receiver is timed with respect to the emission time of the emitted pulses, thus isolating a determined volume of space along the light beam path.

In an embodiment in which a time of flight technique is used, the receiver or light detector is preferably collocated with the emitter or light source 30. In one embodiment, the emitter/receiver (or transceiver) forms a lidar. In one embodiment, the emitter/receiver (or transceiver) forms a monostatic lidar.

In an embodiment in which a time of flight technique is used and in order to isolate the returns from the interaction in the exhaust stream, i.e. the second light, the short light pulses occupy a length substantially equivalent to or shorter than the diameter of the stack in the case of a circular stack if the light pulses propagate through the plume above the center of the stack or shorter than a side of the stack in the case of a square or rectangular stack if the light pulses propagate through the plume parallel to the aforementioned side of the stack. Otherwise, the short light pulses occupy a length substantially equivalent to or shorter than the length of their travel through the plume.

In an embodiment in which they are collocated and scanning is required, both the emitter and receiver are preferably on the same pan and tilt or share the same scanning mirror or mirrors so that the emitter field of regard and the receiver field of view are substantially always aligned together while scanning.

In the case of backscatter lidars, the light source 30 may be adapted to emit very short and intense laser pulses, both for the spatial resolution and for having sufficient return from a small volume, i.e. a small number of scatterers. For example, using sub-nanosecond laser pulses and high speed detection electronics, such as time correlated photon counting, may allow for sufficient spatial resolution for isolating an across stack measurement (integrated path) directly at the output of the stack or for isolating a small volume of the exhaust plume directly at the output of the exhaust stack. For example, one may use 500 picosecond laser pulses that substantially correspond to 7.5 cm of sampling along the laser beam if the detection electronics has a bandwidth that can resolve the laser pulse, such as a few GHz.

As described below, the emitter/receiver may correspond to a DiAL, a fluorescence lidar, a Raman lidar, a gas correlation lidar or the like.

Figure 4:
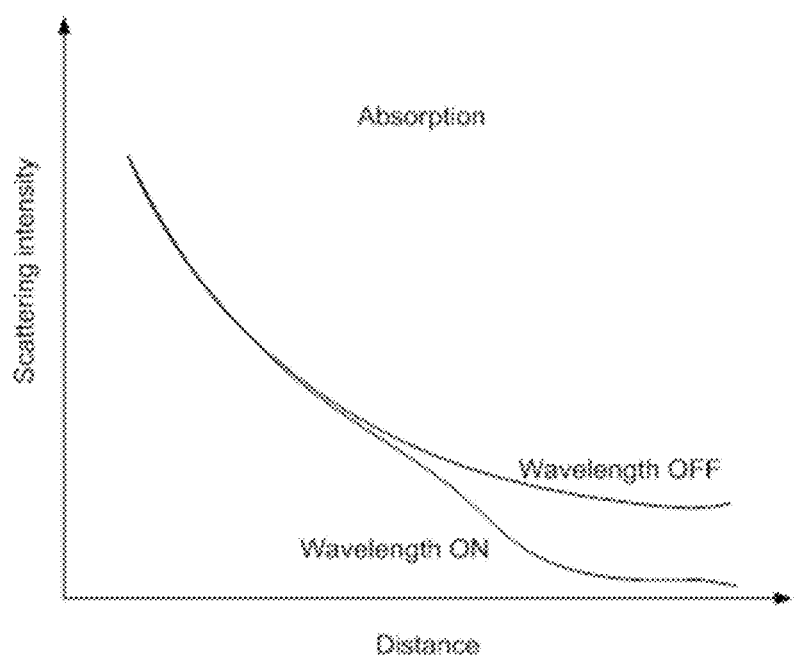
FIG. 4 is an exemplary graph of the optical absorption as a function of a distance for an ON wavelength and an OFF wavelength.

In one embodiment, a DiAL is used for monitoring the portion of the plume being in close proximity to the stack output 38 in order to measure the absorption. In this case, the light backscattered from molecules and particulates is measured along the laser beam path. In one embodiment of a DiAL, elastic scattering is considered. In this case, the energy of the first light beam drops off because of loss caused by scattering and absorption, and the return second light signal at the detector also drops off because of the rise in distance between the lidar and the measured volume along the laser beam. FIG. 4 illustrates the behavior of typical DiAL curves. The concentration of the molecule of interest along the laser beam is retrieved by processing the difference in fall of the signal with distance for different wavelengths. The different wavelengths usually comprise at least an ON absorption wavelength presenting a maximum or strong absorption and an OFF absorption wavelength presenting a minimal or low absorption, for the given molecule to be sensed. It should be understood that, in the case of the use of a DiAL with elastic scattering, the detection wavelength corresponds to the excitation wavelength, i.e. the second light comprises the same wavelengths as those contained in the first light.

Figure 5:
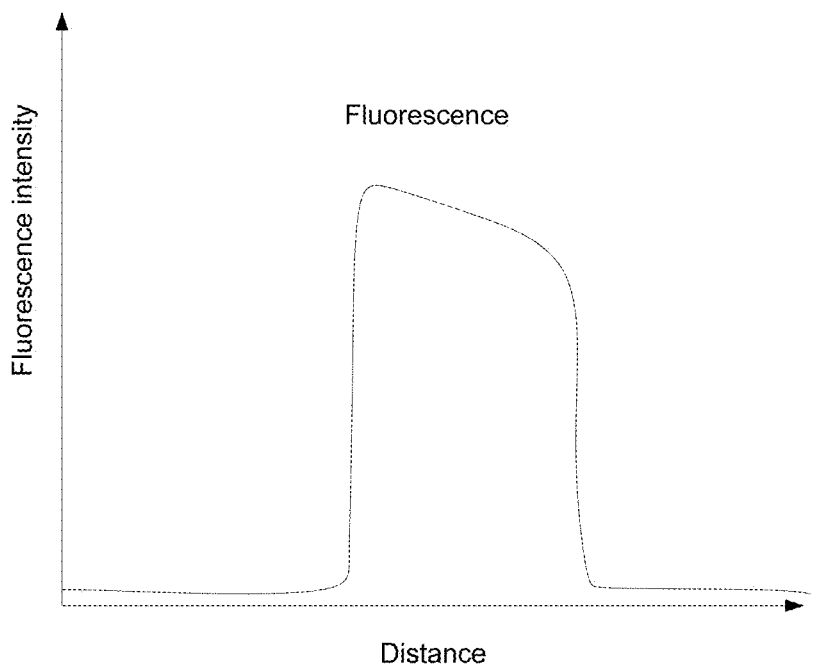
FIG. 5 illustrates an exemplary graph of a pulsed fluorescence intensity as a function of a propagation distance.
Figure 6:
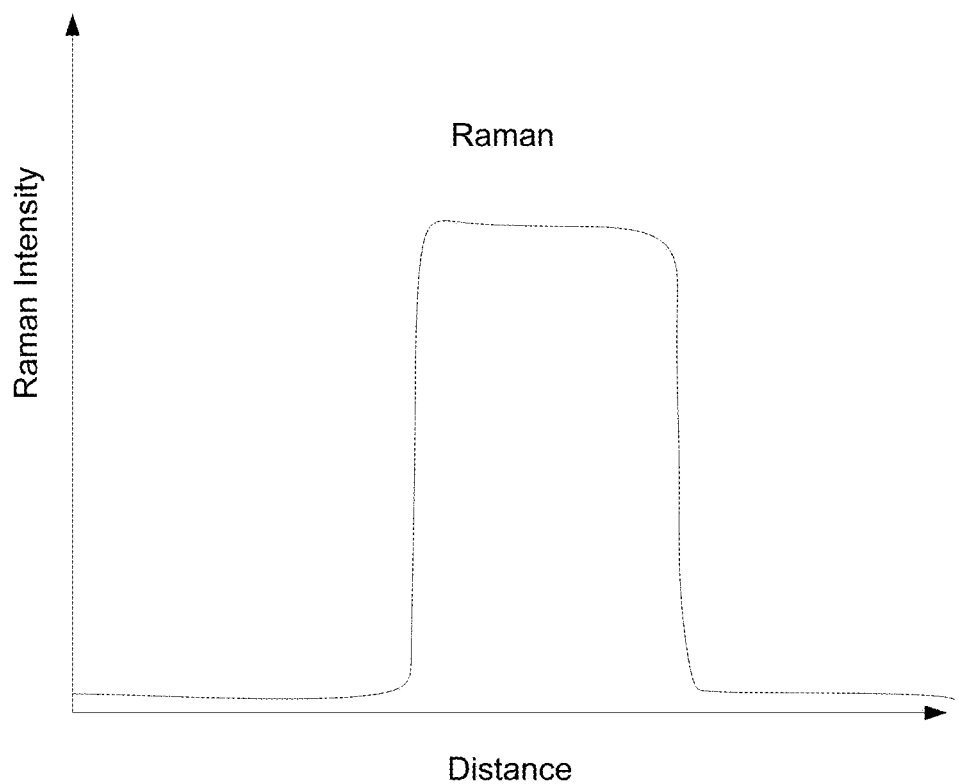
FIG. 6 illustrates an exemplary graph of a pulsed Raman scattering intensity as a function of a propagation distance.

In another embodiment of a DiAL, fluorescence is considered. The person skilled in the art will understand that the fall in the fluorescence signal along the beam represents a measure of the absorption. The rate of fall in the fluorescence signal is equivalent to the rate of fall of the ON wavelength due to absorption and scattering. The Raman signal of say nitrogen on an OFF wavelength will give the loss due to scattering alone. The Raman cross-section is no longer necessary, since only the rate of fall of the signal is of interest. Only the instrument response with respect to distance is required. FIG. 5 illustrates an exemplary spatially resolved fluorescence curve when there is very little of the molecular species of interest outside the exhaust stream or plume.

In a further embodiment of a DIAL, Raman scattering is used for measuring absorption. For example, measuring the Raman return of nitrogen on at least one ON wavelength and the Raman return of nitrogen on at least one OFF wavelength can be used as a measure of absorption for NO. The person skilled in the art will note that the Raman return depends only on molecules, of nitrogen in this case, and not on the particulate loading of the air. The relative concentration of nitrogen is fairly constant everywhere, including in the stack exhaust.

In another embodiment, a fluorescence lidar is used. In this case, the excitation wavelength of the first light is tuned to an absorption peak while the energy of the second light at another fluorescing wavelength is measured, i.e. resonance fluorescence is not considered.

In one embodiment, since fluorescence does not require scattering from particulates or molecules, the signal strength of the second light does not depend on strong particulate loading of the plume volume being probed. Moreover, fluorescence is measured against an essentially zero background, unlike absorption which is a slight fall in signal amplitude between at least two wavelengths. Furthermore, fluorescence is present substantially only in the plume where the concentration of emitted molecules/particulates is much higher than in ambient air. This relaxes the requirement for high spatial resolution measurements.

In one embodiment, the fluorescence quantum yield must be well known in the particular measurement conditions and the first light energy at the site of the measurement must be measured, for example by measuring the Raman return from nitrogen, the cross section of which must also be known.

In a further embodiment, a Raman lidar is used for determining the concentration of molecules. Since each molecule has a fingerprint Raman signature, any molecule may be monitored through its Raman signal, for example by measuring a molecular concentration.

In one embodiment, the Raman scattering cross-sections may be small, and the number of returned photons may be low. Measuring Raman returns of specific molecules in low concentration may require working in the solar blind UV with high power lasers and with long measurement times.

Since Raman scattering does not require a tunable laser, any excitation wavelength generating a Raman return may be used. In one embodiment, a 266 nm laser (fourth harmonic of Nd:YAG laser or equivalent) is used as the light source 30. The return from nitrogen would also be measured in this case, and the relative Raman cross sections of the molecules of interest with respect to the Raman cross section of nitrogen at the excitation wavelength must be known and the instrument calibrated with respect to wavelength. In this case, as in the case with fluorescence, the Raman scattering from the molecules of interest is practically limited to the exhaust emissions stream if the concentration of the molecule of interest is much higher in the exhaust stream than in the ambient air. But unlike DIAL, there are no ON and OFF wavelengths, only the Raman from the molecule or molecules of interest and that from nitrogen. FIG. 5 illustrates an exemplary spatially resolved Raman return when the molecule of interest is much more concentrated in the exhaust emissions stream than in the ambient air.

Figure 3:
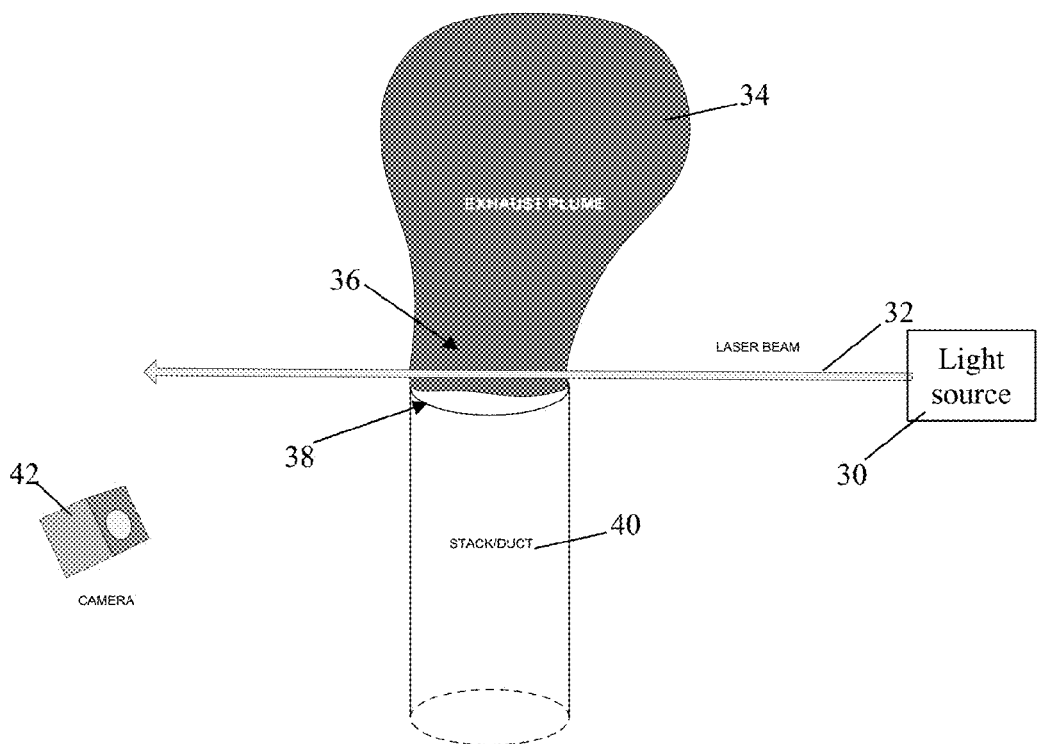
FIG. 3 illustrates a system for remotely monitoring mass emission rates of molecules contained in emissions from a stack using an imaging device, in accordance with an embodiment.

In another embodiment, an imaging device 42 such as a camera is used for imaging the portion of the plume 34 located in the close proximity region 36, as illustrated in FIG. 3. The energy of the scattered light or fluorescence light is then determined using the imaging device 42 and the imaging of the plume 34.

In this case, the imaging device 42 is positioned so that the center of its field of view be at an angle from the excitation light beam. In one embodiment, the angle is chosen to be substantially equal to about 90°. The present method that uses an imaging device 42 such as a camera is referred to as a telemetric lidar technique. The light beam is scattered by molecules and particulates or interacts with the molecules and the same parameter as with the time of flight lidar can be measured, i.e. absorption, fluorescence, or Raman. Spatial information is acquired through the imaging on the different pixels of the imaging device. The imaging device may be a camera with an adequate objective camera lens or a single pixel detector with a small field of view that is scanned over the plume at the output of the exhaust stack. In one embodiment, the pixels of the camera may require a radiometric calibration for an accurate measurement of absorption, fluorescence or Raman scattering along the light beam path. In one embodiment, the distance between the plume and the camera is set to be much larger than the plume size (or exhaust stack diameter) such that the distance from the different points along the light beam path across the plume and the camera is substantially the same. When the angle between the center of the field of view of the imaging device and the excitation light beam is substantially equal to about 90°, all pixels cover substantially the same volume along the light beam path. It should be understood that the first light excitation beam may contain continuous light, continuously modulated light, or pulsed light.

In one embodiment, the imaging device 42 comprises an array of individual detectors or a multi-pixel detector. For example, the imaging device 42 may comprise a linear array of silicon or InGaAs PIN diodes, silicon or InGaAs avalanche photodiodes, photomultipliers, HgCdTe or InSb detectors, or the like. In that case, the size of the field of view of the detectors in the array that is substantially perpendicular to the light beam path may be sufficiently large not to require precise alignment of the field of view in that direction. The size of the field of view of a single detector of the array along the light beam path is smaller than the stack output size along the light beam path. The imaging device 42 may comprise a two-dimensional array of individual detectors. The multi-pixel detector may be a CCD array, a CMOS array, an avalanche HgCdTe array, or the like. The multi-pixel detector may also be an intensified CCD or CMOS. The size of the field of view of a single detector of the two dimensional array or multi-pixel detector along the light beam path is chosen to be smaller than the stack output size along the light beam path.

In the case where the detector system in the receiver is preferably an array of individual detectors or a multi-pixel detector, no scanning of the detector may be required.

If the detector in the receiver is a single pixel detector, then the receiver must be scanned to image successively different volumes along the light beam path inside and outside the exhaust stream. The size of the field of view of the detector perpendicular to the light beam path can be sufficiently large not to require very precise alignment of the field of view in that direction. The size of the field of view along the light beam path must be smaller than the stack/duct/flare's output size along the light beam path.

The person skilled in the art will understand that the above-described monitoring technique may require a spatial resolution such as to resolve a volume along the light beam path the length of which is less than the diameter/side of the stack from which an emissions stream is to be monitored, and may be performed at a large stand-off distance from the stack, such as tens of meters.

The person skilled in the art will also understand that absorption, Raman scattering and induced fluorescence or a mix of these techniques may be used. The measurements can be performed with high spatial resolution lidar techniques or with "imaging" techniques such as telemetric lidar techniques.

The person skilled in the art should further understand that the first light beam can be scanned across the plume at the output of the stack if a mapping of the emissions in the exhaust stream is needed. Scanning of the light beam is preferably done by rotating the light source and associated optics with a pan and tilt unit or with a scanning mirror or scanning mirrors in the path of the light beam in order to scan the cross-section of the plume orthogonal to the emissions flow direction. The scanning apparatus is preferably collocated with the emitter. Other scanning mechanisms may also be used.

As described above, the mass emission rate of a given molecule may be determined using the measurement of optical absorption. Optical absorption can be measured in multiple ways, as known in the art.

In one embodiment, the optical absorption is determined by using the two or more wavelength DIAL technique with at least one ON absorption wavelength and at least one OFF absorption wavelength and measuring the elastic backscattering.

In another embodiment, the optical absorption is determined by using the fluorescence and Raman lidar techniques with an ON absorption wavelength and an OFF absorption wavelength, but instead of measuring the elastic scattering along the light beam, the fluorescence and the Raman scattering at wavelengths different from the excitation wavelength are measured along the light beam. In one embodiment, nitrogen has the advantage of having the same relative concentration everywhere (at a same altitude) and does not depend on the hypothesis of a homogeneous particulate density and size distribution everywhere.

In one embodiment, the fluorescence rate of fall with distance is measured on the ON wavelength to get absorption and scattering losses, and the Raman rate of fall with distance of nitrogen for example is measured on the OFF wavelength to isolate the scattering losses only.

In another embodiment, the Raman rate of fall with distance of nitrogen for example is measured on the ON wavelength and the Raman rate of fall with distance of nitrogen is measured on the OFF wavelength.

In still another embodiment, the optical absorption is determined by measuring absorption in the exhaust stack through the rate of fall with distance of an ON absorption wavelength and the rate of fall with distance of an OFF absorption wavelength through imaging of the light beam.

In one embodiment, the emitter and receiver are positioned in a 90° configuration, i.e. the propagation axis of the first light beam and the axis formed between the detector and the first light beam when in the plume are substantially orthogonal. In this case, the optical absorption is determined by measuring the elastic scattering assuming that the absorption and scattering losses between the interaction volume and the receiver are substantially the same or are otherwise known for all volumes along the light beam path and in the vicinity of the exhaust stream. In another embodiment, the optical absorption is determined by measuring the rate of fall with distance of fluorescence signal when the excitation light beam is on the ON wavelength and the rate of fall with distance of Raman signal of nitrogen for example when the excitation light beam is on the OFF wavelength.

In a further embodiment, the optical absorption is determined by measuring the rate of fall with distance of Raman of nitrogen for example when the excitation light beam is on the ON wavelength and the rate of fall with distance of the Raman signal of nitrogen when the excitation light beam is on the OFF wavelength.

In still another embodiment, the optical absorption is determined using a spectrally broadband light beam and a gas correlation technique and by imaging the elastic scattering in the light beam path with the imaging apparatus. The concentration of the molecule of interest is measured using the correlation strength rate of fall with distance with the gas correlation images, assuming that the absorption losses from the interaction volume to the receiver are substantially the same or are otherwise known for all volumes along the light beam path and in the vicinity of the exhaust stream.

In a further embodiment, the optical absorption is determined using a spectrally broadband light beam and using hyperspectral imaging of the elastic scattering of the light beam using the imaging apparatus, assuming that the absorption losses from the interaction volume to the receiver are substantially the same or are otherwise known for all volumes along the light beam path and in the vicinity of the exhaust stream. This technique is referred to as a differential absorption spectroscopy (DOAS) approach. The concentration of molecules/in the exhaust stream is measured using the rate of fall of the absorption along the light beam path using the measured absorption spectra along the light beam path.

In another embodiment, the optical absorption is determined by imaging the scattering of the light emitted by a tunable light source such as a tunable diode laser along the light beam path with the imaging apparatus and by obtaining the rate of fall of the absorption of the tunable diode laser absorption spectroscopy (TDLAS) signal along the light beam path, assuming that the absorption losses between the interaction volume and the receiver are substantially the same or are otherwise known for all volumes along the light beam path and in the vicinity of the exhaust stream.

As described above, the mass emission rate of a given may also be determined using fluorescence measurements. In this case, it is assumed that the quantum yield for fluorescence is known. The light energy of the first light beam is determined locally along the light beam path by measuring the Raman return of nitrogen for example and using the cross-section for Raman scattering of nitrogen at the excitation wavelength. The detection efficiency of the light detector is known for all measurement volumes along the light beam path and for the measurement wavelengths.

As described above, the mass emission rate of a given molecule may further be determined using Raman scattering measurements. The Raman return for each molecular species of interest is measured with respect to the Raman return of nitrogen for example. The relative Raman cross-sections of the molecular species of interest are known with respect to the Raman cross-section of nitrogen. The receiver detection efficiency is also known for all measurement wavelengths.

Referring back to the prior art remote method described in the background section, this prior art method comprises a plurality of disadvantages. This prior art method teaches to aim at a plume sufficiently dispersed and moving with the wind but not dispersed to the point where the molecular concentrations are not measurable, and thus not fully mixed with the ambient air. Measuring the atmospheric temperature, the pressure and the wind speed and direction with a meteorological weather station is deemed sufficient for the procedures. This is essential for correctly calibrating the absorption measurements. The entire plume must be mapped perpendicularly to the wind direction since the plume size or dispersion is not known a priori. This is time consuming and prone to error because of changing weather parameters (temperature, wind speed, wind direction, rain . . . ). Furthermore, the position of the monitoring device must be changed if the direction of the wind changes. The atmospheric dynamics can also dictate the extent of the mapping in terms of distance and resolution. If the atmospheric conditions change relatively rapidly, the mapping will need to be coarse and the signal to noise ratio far from optimal. This also makes for large measurement errors. Flow speed is taken as constant across the plume and equal to the wind speed measured at ground level in the case of a measurement with a weather station anemometer, which is known to not always be the case. The procedure relies on a minimum of equilibrium between the plume and the atmosphere. This is done in order to minimize gradients of all types (concentration, temperature, flow speed distribution and direction . . . ). Furthermore, this prior art method does not teach how to make measurements in regions of strong gradients or regions in which temperature and flow conditions cannot be inferred using weather station data or usual remote flow speed measurement techniques.

The present method described above makes use of an opposite approach relative to the prior art method. The present method uses the fact that the flow in close proximity to the exhaust stack output and within the exhaust stack diameter is substantially homogeneous and substantially the same as in the exhaust stack close to the output. There is minimal mixing with ambient air. In the case of an exhaust from a combustion stack, the emitted gases are hot and their concentration is substantially equal to that of the gases inside the exhaust stack. In the case of NO for example, the gradients of concentration will be strong at the limits of the plume. This usually requires very high spatial resolution measurements. The wind has no significant effect on flow in the region being in close proximity to the stack output. In the case of a vertical exhaust stack, the flow is essentially vertical. The flow velocity within the close proximity region is substantially the same as that of the flow within the exhaust stack close to the output. The temperature may be measured within the stack close to the output or remotely through optical techniques and within the plume in the close proximity region where the measurements are performed. Since the flow is substantially stable within the close proximity region and the parameters do not change significantly for long periods of time, measurements may be done over extended time periods, which is usually preferred in order to get precise average values. Laser size, weight and power consumption (along with cost) can be reduced substantially. The lidar system can eventually be designed to be transportable, without the need for a dedicated mobile platform as for the prior art method since the position of the lidar system does not have to be changed according to the direction of the wind. Furthermore, mapping the plume is usually not required. The usual large optical scanning subsystem required for mapping the plume while using the prior art method is thus no longer required. A single path measurement may be indicative of the whole plume, whose extent is delimited by the physical stack output. Finally, it is not required that spatial resolution be obtained through high time resolution in time of flight configurations. Spatial resolution may be determined with imaging systems since the concentrations are relatively high (when compared to a dispersed plume), flow is well contained and flow is stable for long periods of time.

While in FIG. 1 the measurement of the flow velocity is performed before the detection of the second light, it should be understood that other embodiments are possible. For example, the detection of the second light may be first performed and the measurement of the flow velocity may occur after the detection of the second light. In another example, the detection of the second light and the measurement of the flow velocity may be performed substantially concurrently.

The embodiments of the invention described above are intended to be exemplary only. The scope of the invention is therefore intended to be limited solely by the scope of the appended claims.

The invention claimed is:

1. A method for remotely monitoring an exhaust plume emitted by an exhaust stack, the method comprising:
    determining a velocity of a flow of the exhaust plume at an output of the exhaust stack, the exhaust plume comprising emissions, the emissions comprising at least one molecule;
    remotely propagating a first light within the exhaust plume emitted by the exhaust stack, the first light being propagated in close proximity to the output of the exhaust stack;
    remotely detecting a second light emitted by the exhaust plume present in close proximity to the output of the exhaust stack and measuring an energy of the detected second light, the second light resulting from an interaction of the first light with the emissions contained within the exhaust plume;
    determining a mass emission rate of the at least one molecule contained in the exhaust plume using the measured energy of the detected second light, the velocity of the flow of the exhaust plume, and a surface area of the exhaust plume at the output of the exhaust stack, the surface area being orthogonal to a direction of the flow of the exhaust plume; and
    outputting the determined mass emission rate.

2. The method of claim 1, wherein the surface area of the exhaust plume substantially corresponds to a surface area of the output of the exhaust stack.

3. The method of claim 1, wherein the surface area of the exhaust plume is taken in a plane substantially perpendicular to a direction of the flow of the exhaust plume.

4. The method of claim 1, wherein said determining the velocity comprises measuring the velocity within the exhaust stack using a flow velocity sensor installed within the exhaust stack.

5. The method of claim 1, wherein said determining the velocity comprises measuring the velocity outside the exhaust stack in a region being in close proximity to the output of the exhaust stack.

6. The method of claim 5, wherein said measuring the velocity is remotely and optically performed.

7. The method of claim 1, wherein the exhaust stack is connected to a combustion chamber in which a mixture of fuel and air is burnt and said determining the velocity comprises calculating the velocity using at least a flow rate of the fuel delivered to the combustion chamber, a flow rate of the air delivered to the combustion chamber, a composition of the fuel, and a temperature within the combustion chamber.

8. The method of claim 1, wherein said detecting the second light comprises detecting the second light that propagates back towards a transceiver adapted to emit the first light and detect the second light.

9. The method of claim 1, wherein said detecting the second light comprises imaging the second light in the exhaust plume being in close proximity to the output of the exhaust stack.

10. The method of claim 9, wherein the first and second lights each comprise one of a pulsed light, a continuous light, and a continuous modulated light.

11. The method of claim 1, wherein said determining the mass emission rate comprises:
    determining a differential optical absorption of the first light being in close proximity to the output of the exhaust stack;
    determining a concentration of the at least one molecule using the differential optical absorption; and determining the mass emission rate using the concentration, the velocity of the flow of the exhaust plume, and the surface area of the exhaust plume.

12. The method of claim 11, wherein said determining the absorption is performed using a differential absorption lidar.

13. The method of claim 11, wherein said determining the absorption is performed using one of a fluorescence lidar and a Raman lidar.

14. The method of claim 1, wherein said detecting said second light comprises detecting Raman scattered light generated by the exhaust plume while interacting with the first light being propagated in close proximity to the output of the exhaust stack, and said determining the mass emission rate comprises:

determining a concentration of the at least one molecule using relative Raman scattered light energies; and determining the mass emission rate using the concentration, the velocity of the flow of the exhaust plume, and the surface area of the exhaust plume.

15. The method of claim 1, wherein said detecting said second light comprises detecting fluorescence light generated by the exhaust plume while interacting with the first light being propagated in close proximity to the output of the exhaust stack, and said determining the mass emission rate comprises:

determining a concentration of the at least one molecule using fluorescence energy relative to a local excitation energy; and determining the mass emission rate using the concentration, the velocity of the flow of the exhaust plume, and the surface area of the exhaust plume.

16. A system for remotely monitoring an exhaust plume emitted by an exhaust stack, the system comprising:

a flow velocity unit for determining a velocity of a flow of the exhaust plume at an output of the exhaust stack, the exhaust plume comprising emissions, the emissions comprising at least one molecule;

a light source for generating a first light, the light source being adapted to propagate the first light within a portion of the exhaust plume emitted by the exhaust stack being in close proximity to the output of the exhaust stack;

a light detection device for detecting a second light emitted by the exhaust plume present in close proximity to the output of the exhaust stack and measuring an energy of the detected second light, the second light resulting from an interaction of the first light with the emissions contained within the exhaust plume; and a calculation module for determining a mass emission rate of the at least one molecule contained in the exhaust plume using the measured energy of the detected second light, the determined velocity of the flow of the exhaust plume, and surface area of the exhaust plume at the output of the exhaust stack, the surface area being orthogonal to a direction of the flow of the exhaust plume, and outputting the determined mass emission rate.

* * * * *